United States Patent [19]
Avruch et al.

[11] Patent Number: 6,103,692
[45] Date of Patent: Aug. 15, 2000

[54] INHIBITING PROTEIN INTERACTIONS

[75] Inventors: Joseph Avruch, Brookline; Zhujun Luo, Chestnut Hill, both of Mass.; Mark S. Marshall, Carmel, Ind.

[73] Assignee: The General Hospital Corporation, Boston, Mass.

[21] Appl. No.: 08/814,836

[22] Filed: Mar. 11, 1997

Related U.S. Application Data

[60] Provisional application No. 60/013,274, Mar. 12, 1996.

[51] Int. Cl.[7] .................................................. A61K 38/00
[52] U.S. Cl. ............................... 514/12; 514/13; 514/14; 514/15
[58] Field of Search .......................................... 514/12–15

[56] References Cited

U.S. PATENT DOCUMENTS

| 5,582,995 | 12/1996 | Avruch et al. | 435/71 |
| 5,597,719 | 1/1997 | Freed et al. | 435/194 |

FOREIGN PATENT DOCUMENTS 29727  12/1994  WIPO.

OTHER PUBLICATIONS

Andersson et al., "Cloning, Structure, and Expression of the Mitochondrial Cytochrome P–450 Sterol 26–Hydro–xylase, a Bile Acid Biosynthetic Enzyme", *J. Biol. Chem.,* 264:8222–29 (1989).

Avruch et al., "Raf meets Ras: Completing the Framework of a Signal Transduction Pathway", *TIBS,* 19:279–83 (1994).

Barnard et al., "Identification of the Sites of Interaction Between c–Raf–1 and Ras–GTP", *Oncogene,* 10:1283–90 (1995).

Bodor et al., "A Strategy for Delivering Peptides into the Central Nervous System by Sequential Metabolism", *Science,* 257:1698–1700 (1992).

Brtva et al., "Two Distinct Raf Domains Mediate Interaction with Ras", *J. Biol. Chem.,* 270:9809–12 (1995).

Cadwallader et al., "N–Terminally Myristoylated Ras Proteins Require Palmitoylation or a Polybasic Domain for Plasma Membrane Localization", *Mol. and Cell. Biol.,* 14(7):4722–30 (1994).

Chow et al., "Functional Mapping of the N–terminal Regulatory Domain in the Human Raf–1 Protein Kinase", *J. Biol. Chem.,* 270:14100–106 (1995).

Chuang et al., "Critical Binding and Regulatory Interactions Between Ras and Raf Occur Through a Small, Stable N–terminal Domain of Raf and Specific Ras Effector Residues", *Mol. Cell. Biol.,* 14:5318–25 (1994).

Friden et al., "Blood–Brain Barrier Penetration and in Vivo Activity of an NGF Conjugate", *Science,* 259:343–77 (1993).

Fridman et al., "The Minimal Fragments of c–Raf–1 and NF1 That Can Suppress v–Ha–Ras–induced Malignant Phenotype", *J. Biol. Chem.,* 269:30105–108 (1994).

Ghosh et al., "Identification of Discrete Segments of Human Raf–1 Kinase Critical for High Affinity Binding to Ha–Ras", *J. Biol. Chem.,* 269:30785–88 (1994).

Ghosh et al., "The Cysteine–rich Region of Raf–1 Kinase Contains Zinc, Translocates to Liposomes, and is Adjacent to a Segment that Binds GTP–Ras", *J. Biol. Chem.,* 269:10000–7 (1994).

Guan et al., "Eukaryotic Proteins Expressin in *Escherichia coli*: An Improved Thrombin Cleavage and Purification Procedure of Fusion Proteins with Glutathione S–Transferase", *Anal. Biochem.,* 192:262–76 (1991).

Häfner et al., "Mechanism of Inhibition of Raf–1 by Protein Kinase A", *Mol. and Cell Biol.,* 14:6696–703 (1994).

Herrmann et al., "Quantitative Analysis of the Complex Between $p21^{ras}$ and the Ras–binding Domain of the Human Raf–1 Protein Kinase", *J. Biol. Chem.,* 270:2901–905 (1995).

Hu et al., "Cysteine–rich Region of Raf–1 Interacts with Activator Domain of Post–translationally Modified Ha–Ras", *J. Biol. Chem.,* 270(51):30274–77 (1995).

Kyriakis et al., "Mitogen Regulation of c–Raf–1 Protein Kinase Activity Toward Mitogen–activated Protein Kinase–kinase", *J. Biol. Chem.,* 268:16009–19 (1993).

Leevers et al., "Requirement for Ras in Raf Activation is Overcome by Targeting Raf to the Plasma Membrane", *Nature,* 369:411–14 (1994).

Luo et al., "Identification of the 14.3.3 ζ Domains Important for Self–association and Raf Binding", 270:23681–687 (1995).

Marble et al., "Peptides Block Ras Function; Potentially Blocks Oncogenic Development", *Cancer Biotech Weekly,* p. 6(1), (1996).

McGeady et al., "The Farnesyl Group of H–Ras Facilitates the Activation of a Soluble Upstream Activator of Mitogen–activated Protein Kinase", *J. Biol. Chem.,* 270:26347–51 (1995).

Nassar et al., "The 2.2 Å Crystal Structure of the Ras–binding Domain of the Serine/Threonine Kinase c–Raf–1 in Complex with Rap 1A and a GTP Analogue", *Nature,* 375:554–60 (1995).

Niehof et al., "A Small Peptide Derived from the Aminoterminus of c–Raf–1 Inhibits c–Raf–1/Ras Binding", *Biochem. and Biophys. Res. Comm.,* 206:46–50 (1995).

(List continued on next page.)

*Primary Examiner*—Sheela Huff
*Attorney, Agent, or Firm*—Fish & Richardson, P.C.

[57] ABSTRACT

The invention discloses methods of inhibiting direct binding of Ras with Raf and screening methods to identify compounds which inhibit direct binding of Ras to Raf, Raf activation, and cell proliferation.

7 Claims, 8 Drawing Sheets

OTHER PUBLICATIONS

Okada et al., "Post–translational Modification of H–Ras is Required for Activation of, but not for Association with, B–Raf", *J. Biol. Chem.*, 271:4671–78 (1996).

Quest et al., "A Phorbol Ester Binding Domain of Protein Kinase Cγ, Deletion Analysis of the Cys2 Domain Defines a Minimal 43–Amino Acid Peptide", *J. Biol. Chem.*, 269:2961–70 (1994).

Vjotek et al., "Mammalian Ras Interacts Directly with the Serine/Threonine Kinase Raf", *Cell*, 74:205–14 (1993).

Warne et al., "Direct Interaction of Ras and the Amino–terminal Region of Raf–1 In Vitro", *Nature*, 364:352–55 (1993).

Yamamori et al., "Purification of a Ras–dependent Mitogen–activated Protein Kinase Kinase Kinase from Bovine Brain Cytosol and its Identification as a Complex of B–Raf and 14–3–3 Proteins", *J. Biol. Chem.*, 270:11723–26 (1995).

Zhang et al., "Normal and Oncogenic $p21^{ras}$ Proteins Bind to the Amino–terminal Regulatory Domain of c–Raf–1", *Nature*, 364:308–13 (1993).

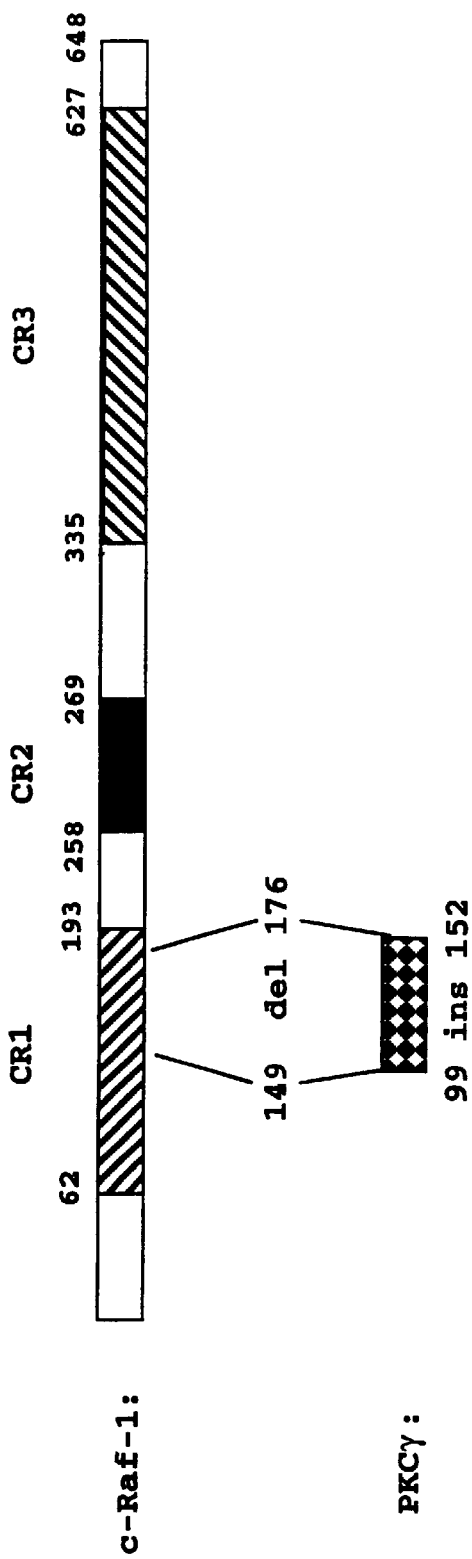

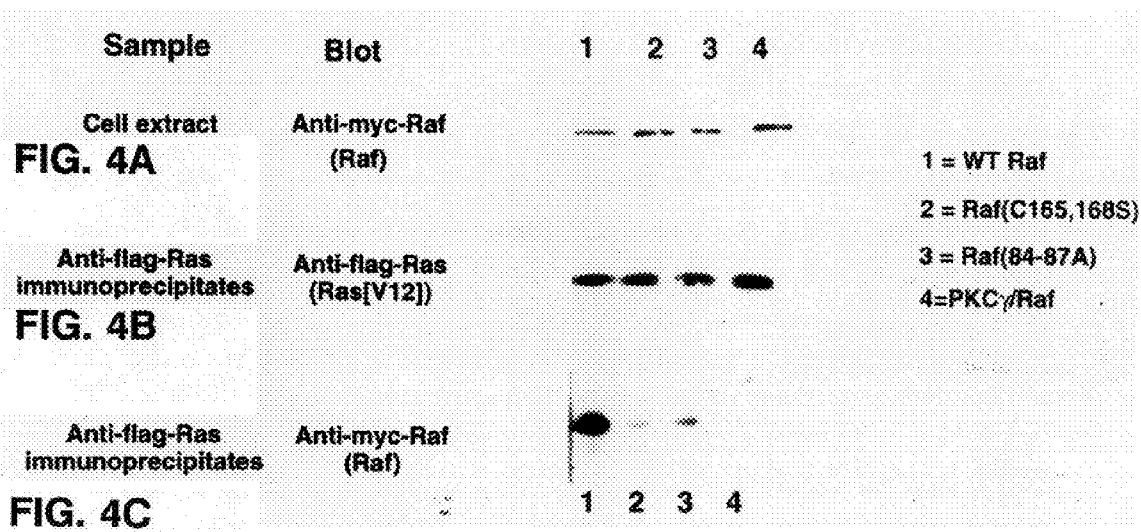

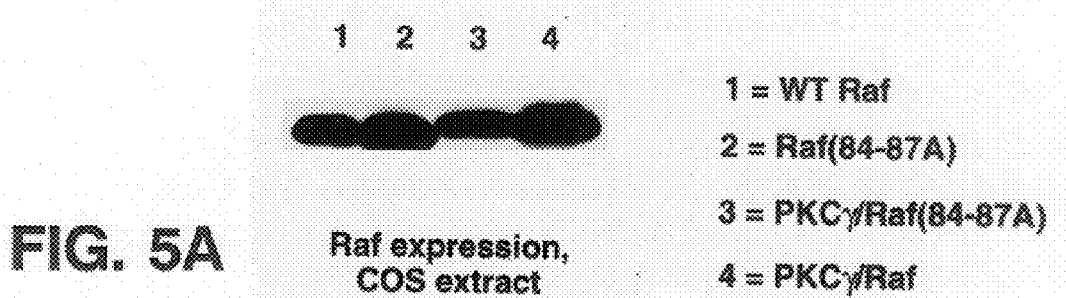
FIG. 5A  Raf expression, COS extract
1 = WT Raf
2 = Raf(84-87A)
3 = PKCγ/Raf(84-87A)
4 = PKCγ/Raf
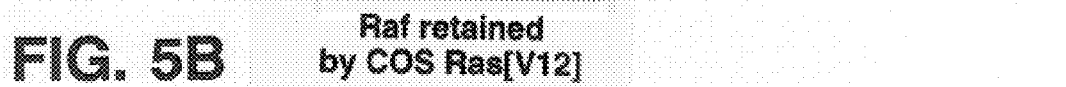
FIG. 5B  Raf retained by COS Ras[V12]
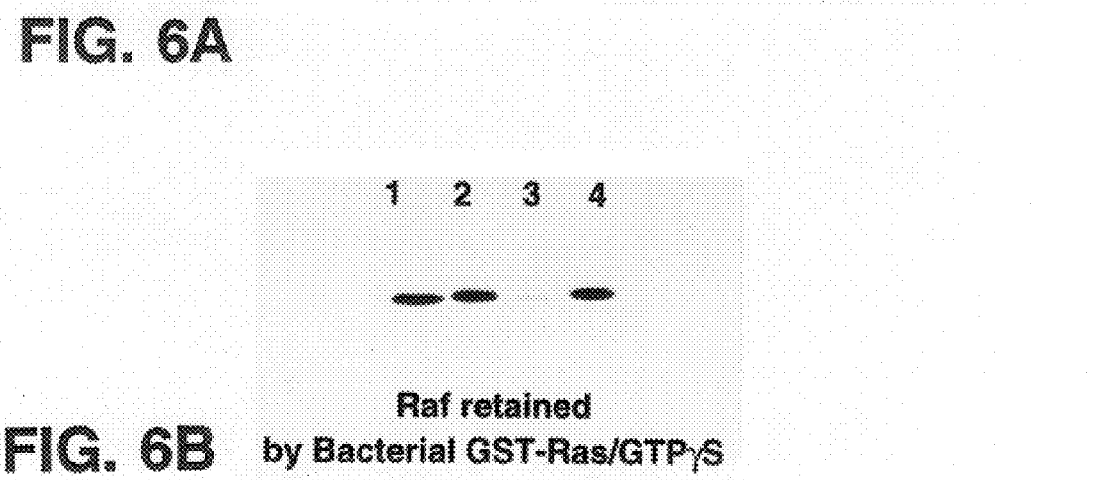
FIG. 6A  Raf expression, COS extract
1 = WT Raf
2 = Raf(C165,168S)
3 = Raf(84-87A)
4 = PKCγ/Raf
FIG. 6B  Raf retained by Bacterial GST-Ras/GTPγS

INHIBITING PROTEIN INTERACTIONS

CROSS REFERENCE TO RELATED APPLICATIONS

This application claims priority from provisional application Ser. No. 60/013,274, filed on Mar. 12, 1996.

STATEMENT AS TO FEDERALLY SPONSORED RESEARCH

This invention was made with Government support under DK41513 and DK41762 awarded by the National Institutes of Diabetes and Digestive and Kidney Diseases. The Government has certain rights in the invention.

BACKGROUND OF THE INVENTION

The invention relates to signal transduction.

The ras gene was discovered as an oncogene of the Harvey (rasH) and Kirsten (rasK) rat sarcoma viruses. In humans, characteristic mutations in the cellular ras gene (c-ras) have been associated with many different types of cancers. These mutant alleles, which render Ras constitutively active, have been shown to transform cells, such as the murine cell line NIH 3T3, in culture.

The ras gene product binds to guanine triphosphate (GTP) and guanine diphosphate (GDP) and hydrolyzes GTP to GDP. It is the GTP-bound state of Ras (Ras-GTP) that is active. An accessory molecule, GTPase-activating protein (GAP) also binds to Ras and accelerates the hydrolysis of GTP. The ras proto-oncogene requires a functionally intact raf-1 proto-oncogene in order to transduce growth and differentiation signals initiated by receptor and non-receptor tyrosine kinases in higher eukaryotes. Activated Ras is necessary for the activation of the c-raf-1 proto-oncogene, but the biochemical steps through which Ras activates the Raf-1 protein (Ser/Thr) kinase are not well characterized.

SUMMARY OF THE INVENTION

It has now been discovered that Raf binds to Ras-GTP through two relatively independent interactions. Raf amino acids 50–150 (SEQ ID NO:5) bind to the Ras effector loop (Ras residues 32–40; SEQ ID NO:3) and the Raf zinc finger domain binds to an epitope present only in prenylated Ras. These interactions participate in the transduction of an intracellular signal via the Ras-Raf mediated signal transduction pathway which culminates in cell proliferation.

Accordingly, the invention features a method of reducing proliferation of cells in a mammal which includes the steps of administering to the mammal, or contacting the cells with, a compound which inhibits direct binding of a non-effector loop domain of Ras, e.g., a portion of Ras which is distinct from the effector loop domain and contains a prenylated epitope, with a zinc finger domain of Raf. Preferably, the mammal is a human and the compound reduces Raf enzymatic activity, e.g., Raf kinase activity. The compound may be a zinc finger domain-containing polypeptide, such as a polypeptide containing the consensus amino acid sequence of HXXXXXXXXXXXCXXCXXXXXXXXXC XXCXXXXHXXCXXXXXXXC (SEQ ID NO:1) where X can be any amino acid, e.g., a polypeptide containing the zinc finger domain of Raf, amino acids 139–184 of Raf (HNFARKTFLKLAFCDICQKFLLNGFRCQTCGYKFHE HCSTKVPTMC; SEQ ID NO:2). In another embodiment, the compound includes a lipid moiety which binds to a zinc finger domain of Raf. Preferably, the lipid moiety is a farnesyl moiety For example, the compound may contain a carboxyterminal fragment of Ras which contains a carboxyterminal farnesyl moiety at position $C_{186}$.

The method may also include the step of administering to the mammal or contacting the cells with a second, different compound which inhibits direct binding of the effector loop domain of Ras with an amino-terminal Ras-binding domain of Raf. For example, the compound may be a polypeptide containing the effector loop domain of Ras, e.g., amino acids 32–40 of Ras (YDPTIEDSY; SEQ ID NO:3). In other embodiments, the compound may be a polypeptide containing amino acids 84–87 of Raf (KALK; SEQ ID NO:4) or a polypeptide containing amino acids 50–150 of Raf (DPSKTSNTIRVFLPNKQRTVVNVRNGMSLHDCL MKALKVRGLQPECCAVFRLLHEHKGKKARLDWN TDAASLIGEELQVDFLDHVPLTTHNFARKTFLKLA; SEQ ID NO:5).

The invention also features a method of screening candidate compounds to identify a compound capable of inhibiting direct binding of Ras to Raf which includes the steps of (a) providing a zinc finger domain-containing fragment of Raf; (b) providing a Raf-binding fragment of Ras; (c) contacting the zinc finger domain-containing fragment of Raf or the Raf-binding fragment of Ras with a candidate compound; and (d) determining the binding of the zinc finger domain-containing fragment of Raf and the Raf-binding fragment of Ras. The Raf fragment may first be contacted with the compound, followed by contact with the Ras fragment and subsequent measurement of Ras-Raf binding. Alternatively, the Ras fragment may first be contacted with the compound, followed by contact with the Raf fragment and subsequent measurement of Ras-Raf binding. In another variation of the assay, the Ras fragment, Raf fragment and the candidate compound may all be incubated together simultaneously, followed by measurement of Ras-Raf binding. In another variation, Ras and Raf may be allowed to bind and then contacted with the compound, after which Ras-Raf binding is measured. In this manner, the ability of the compound to disrupt pre-bound Ras-Raf may be evaluated. In vitro and/or in situ Ras-Raf binding may be measured using a variety of methods known in the art, such as coimmunoprecipitation. A decrease in binding in the presence of the compound compared to that in the absence of the compound indicates that the compound inhibits direct binding of Ras to Raf. Preferably, the zinc finger domain-containing fragment of Raf comprises the amino acid sequence of SEQ ID NO:1; more preferably, the Raf fragment includes the amino acid sequence of SEQ ID NO:2. The Raf-binding fragment of Ras is preferably post-translationally modified to add a lipid moiety such as a farnesyl moiety, e.g., a farnesyl moiety located at position $C_{186}$ of eukaryotic prenylated Ras.

The invention also includes a method of screening candidate compounds to identify a compound capable of inhibiting Raf activation which includes the steps of (a) providing a fragment of Raf comprising a zinc finger domain, e.g., a CR1 domain containing an intact zinc finger domain, and a kinase catalytic domain, e.g, the CR3 domain of Raf; (b) providing a Raf-binding fragment of Ras, e.g, a GTP-bound prenylated fragment of Ras; (c) contacting the fragment of Raf or Raf-binding fragment of Ras with a candidate compound; and (d) determining the Raf kinase activity of the Raf fragment. A decrease in activity in the presence of the compound compared to that in the absence of the compound indicates that the compound inhibits Raf activation.

Also within the invention is a method of screening candidate compounds to identify a compound capable of inhibiting cell proliferation, e.g., proliferation associated with transformed cells, i.e., cancer cells, which includes the steps of (a) providing a cell transfected with a substantially pure DNA encoding a transformation-competent Ras such as Ha-Ras (V12), Ras CaaX, or myristoylated Ras; (b) contacting the cell with a candidate compound; and (c) determining the amount of proliferation of the cell. For example, the cell may be a fibroblast cell, and cell proliferation may be evaluated by measuring foci formation of the cells, an indication of cell transformation. A decrease in cell proliferation in the presence of the candidate compound compared to that in the absence of the candidate compound indicates that the candidate compound inhibits cell proliferation, e.g., unwanted proliferation such as that associated with cancerous, i.e., transformed cells.

"Substantially pure" as used herein refers to a DNA which has been purified from the sequences which flank it in a naturally occurring state, i.e., a DNA fragment which has been removed from the sequences which are normally adjacent to the fragment, e.g., the sequences adjacent to the fragment in the genome in which it naturally occurs, and which has been substantially purified from other components which naturally accompany the DNA, e.g., DNA which has been purified from the proteins which naturally accompany it in the cell.

Other features and advantages of the invention will be apparent from the following detailed description and from the claims.

DETAILED DESCRIPTION

The drawings will first be briefly described.
Drawings

FIG. 1A is a diagram showing the structure of c-Raf-1 and chimeric protein kinase C (PKC)γ/Raf with conserved domains CR1, CR2, and CR3. CR1 encompasses most of the Ras binding domain (amino acids 50–150; SEQ ID NO:5) which binds to the effector loop domain of Ras and overlaps with the cysteine-rich region, Raf amino acids 139–184 (SEQ ID NO:2). CR2 is Ser-Thr rich, and CR3 encompasses the kinase catalytic domain.

FIG. 1B is a diagram showing an alignment of the zinc finger domains of c-Raf-1 and PKCγ. The conserved Cys and His residues in the two zinc fingers have been aligned and are shown in bold type. The amino acid sequence of the chimeric γ/Raf protein is indicated: to construct chimeric γ/Raf, DNA sequences encoding Raf amino acids 150–177 (AFCDICQKFLLNGFRCQTCGYKFHEHCS; SEQ ID NO:6) were deleted, and replaced with the zinc finger domain of PKCγ (amino acids 99–152 of PKCγ; RNKHKFRLHSYSSPTFCDHCGSLLYGLVHQG-GMKCSCCEMNVHRRCVRSVPSLCG; SEQ ID NO:7).

FIG. 2A is a bar graph showing activation of wildtype and zinc finger variants of Raf by epidermal growth factor (EGF) and phorbol myristate acetate (PMA). COS M7 cells were transfected with 5 μg of cDNA encoding Myc-tagged versions of wildtype c-Raf-1 (lanes 1–3), Raf (C165, 168S) (lanes 4–6), γ/Raf chimera (lanes 7–9), and a γ/Raf chimera with inactivating mutations in the γ zinc finger (lanes 10–12). Thirty hours after transfection, cells were deprived of serum for 16 hours, followed by the addition of EGF (50 ng/ml; lanes 2, 5, 18, 11) and PMA (1 μM; lanes 3, 6, 9 and 12) or carrier (control; lanes 1, 4, 7, 10). The cells were extracted 15 minutes. The recombinant Raf polypeptides were immunoprecipitated by anti-Myc monoclonal antibody 9B7.3. The kinase assay was performed by sequential incubation of the immune complex retained on protein G-sepharose beads with GST-MEK1 and Erk-1. The $^{32}$P-labeled polypeptides were resolved on SDS-PAGE, transferred to PVDF membrane and visualized by autoradiography using anti-Myc monoclonal antibody 9E10.2. The $^{32}$P-Erk-1 was measured by liquid scintillation counting of the excised band.

Figure 2A:
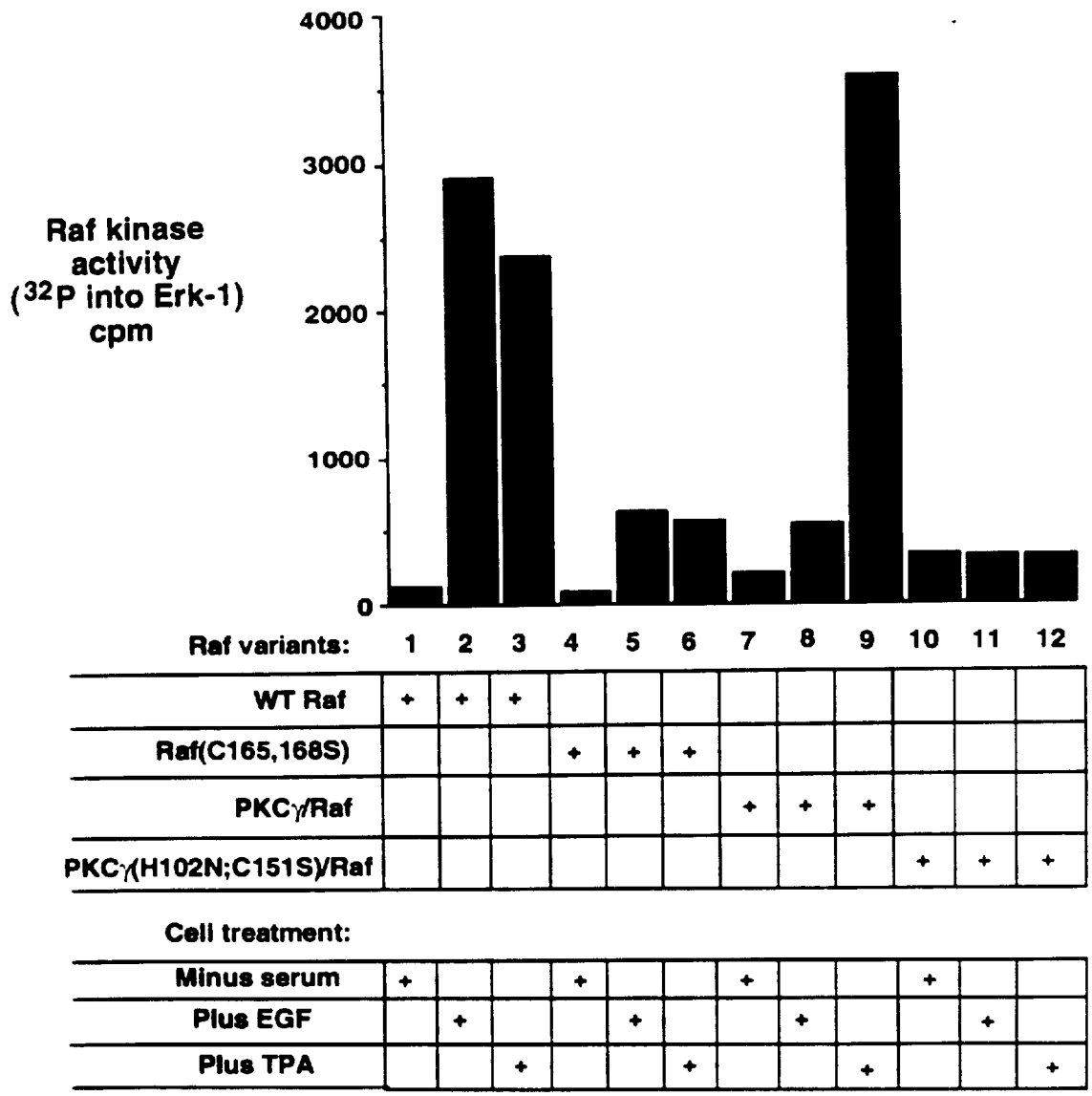
FIG. 2B is an autoradiograph showing incorporation of $^{32}$p into MEK-1 and Erk-1.
FIG. 2C is a photograph of an immunoblot.
FIG. 2D is a bar graph showing PMA activation of γ/Raf. COS cells expressing Myc-Raf (solid bars) or γ/Raf (open bars) were treated with PMA (1 μM) for 1 or 24 hours; the latter cells were then restimulated with PMA or EGF for an additional 15 minutes.
Figure 2B:
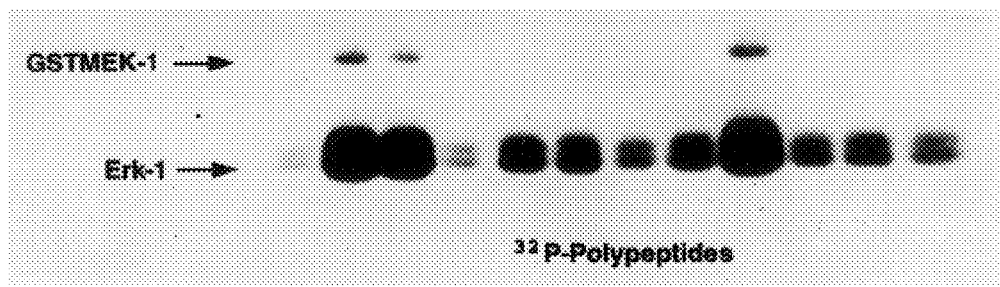
Figure 2C:
Figure 3B:
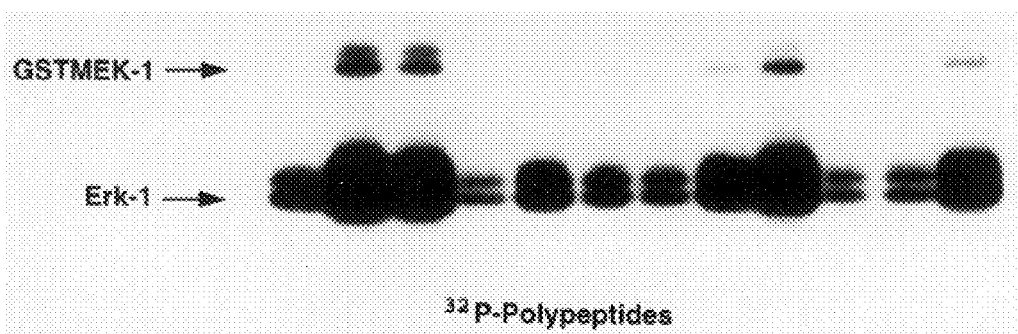
Figure 3C:
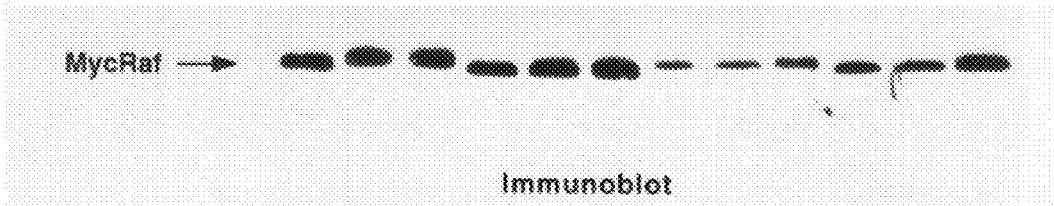
Figure 2D:
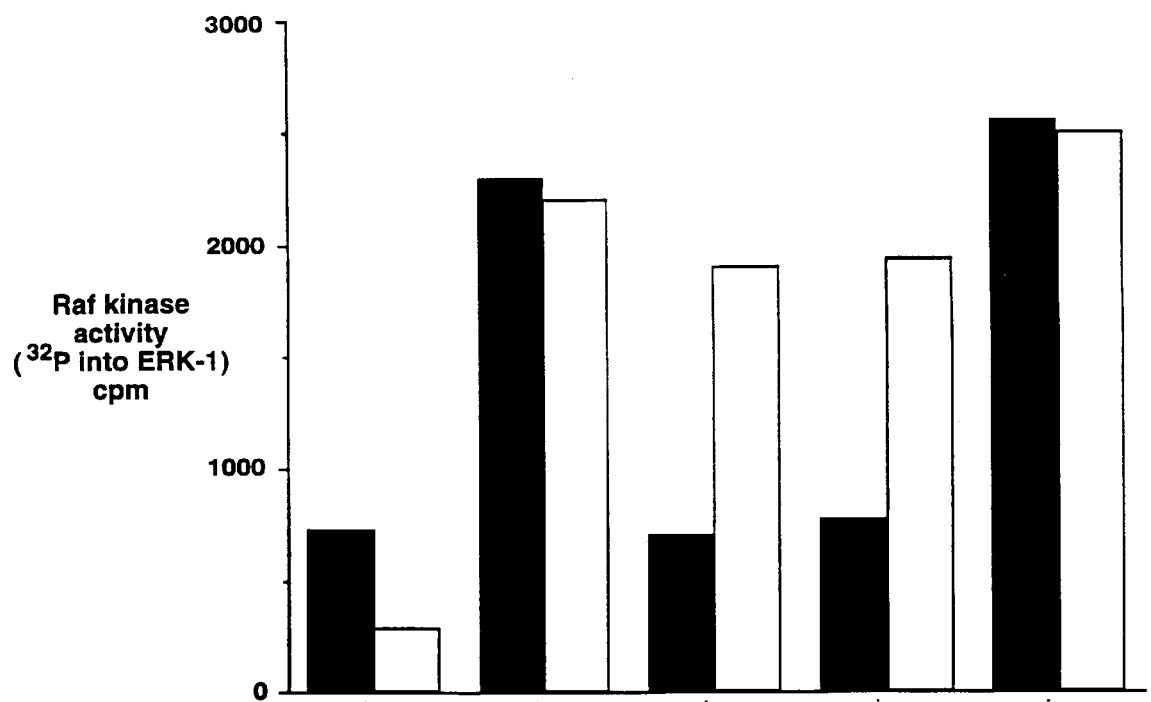
Figure 3A:
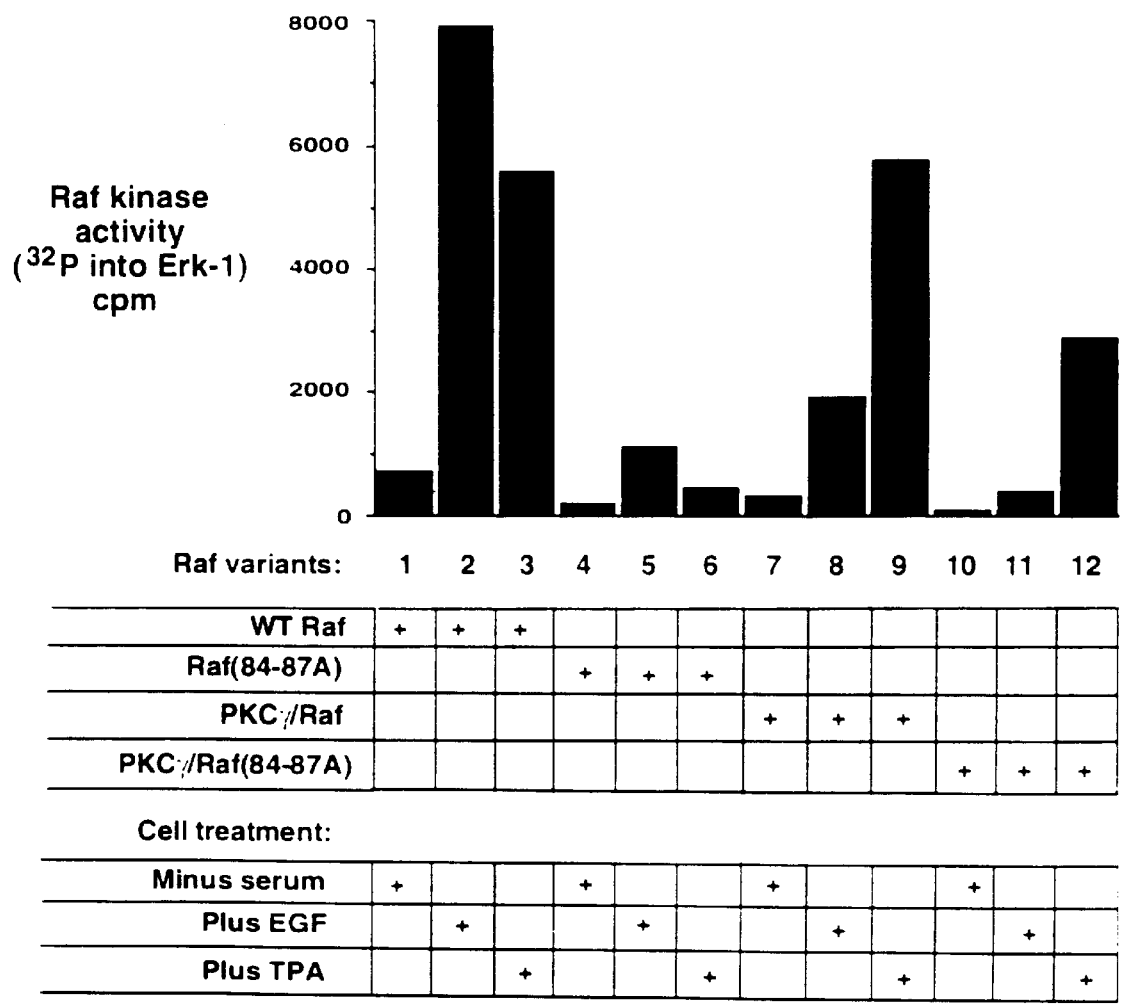

FIG. 3A is a bar graph showing the importance of Raf binding to the Ras effector loop in the activation of wildtype Raf and γ/Raf. cDNAs were transfected into COS M7 cells: wildtype Raf (lanes 1–3; Raf (84–87A) (lanes 4–6); γ/Raf (lanes 7–9); and γ/Raf (84–87A) (lanes 10–12). Cells deprived of serum for 18 hrs were stimulated by treatment with EGF, 50 ng/ml (lanes 2, 5, 8, 11), PMA, 1 μM (lanes 3, 6, 9, 12) or carrier (control; lanes 1, 4, 7, 10) for 15 min. prior to extraction.

FIG. 3B is an autoradiograph showing incorporation of $^{32}$P into MEK-1 and Erk-1.

FIG. 3C is a photograph of an immunoblot.

FIG. 4A is a photograph of an anti-Myc immunoblot (9E10.2) of Myc-Raf variants in the COS cell extracts.

FIG. 4B is a photograph of an anti-FLAG-Ras immunoblot of the anti-FLAG antibody M2 immunoprecipitate recovered on protein G sepharose.

FIG. 4C is a photograph of an anti-Myc immunoblot (9E10.2) of the anti-FLAG M2 immunoprecipitate. For the experiments shown in FIGS. 4A–4C, each of the cDNAs encoding the Myc-Raf variants (5 μg) was cotransfected with FLAG-Ha-Ras (V12) (5 μg) into COS cells. Cells were extracted 48 hours after transfection. The recombinant FLAG-Ras was purified using anti-FLAG monoclonal antibody M2 and protein G sepharose. The immune complex was resolved by SDS-PAGE and subjected to immunoblotting.

FIG. 5A is an anti-Myc immunoblot (9E10.2) of cell extracts (0.1 mg protein) prepared from cells transfected with Myc-Raf variants.

FIG. 5B is an anti-Myc immunoblot of the polypeptide complex retained by immobilized COS recombinant Ras (V12). For FIGS. 5A and 5B, the cDNA encoding FLAG Ha-Ras (V12) was transfected into COS cells. Cell extracts were prepared 48 hours thereafter, and aliquots containing 2 mg protein were subjected to immunoprecipitation with anti-FLAG monoclonal antibody M2. After purification on protein G-sepharose, the immobilized COS recombinant Ras was labeled with γ-S-GTP and incubated at 4° C. for 1 hour with an aliquot of an extract prepared from COS cells transfected 48 hours previously with cDNA encoding the Myc Raf variants indicated; each aliquot contained 1 mg total protein. After three washes with lysis buffer, the polypeptide complexes were subjected to SDS PAGE and immunoblotting.

FIG. 6A is an anti-Myc immunoblot (9E10.2) of the extracts (0.1 mg protein) prepared from cells transfected with Myc-Raf variants.

FIG. 6B is an anti-Myc immunoblot of the polypeptide complex retained by immobilized bacterial GST-Ras/GTPγS. For FIGS. 6A and 6B, prokaryotic recombinant GST-Ha-Ras was labeled with γ-S-GTP. Aliquots containing 5 μg protein were incubated with aliquots of cell lysates (containing 1 mg protein) of COS cells transiently expressing the Myc Raf variants. After 1 hr at 4° C., the complexes were adsorbed by glutathione Sepharose 4B, washed thrice, subjected to SDS-PAGE and immunoblotted with anti-Myc antibody (9E10.2) to detect the Myc-Raf polypeptides that associate with GST Ras-GTP.

Figure 7A:
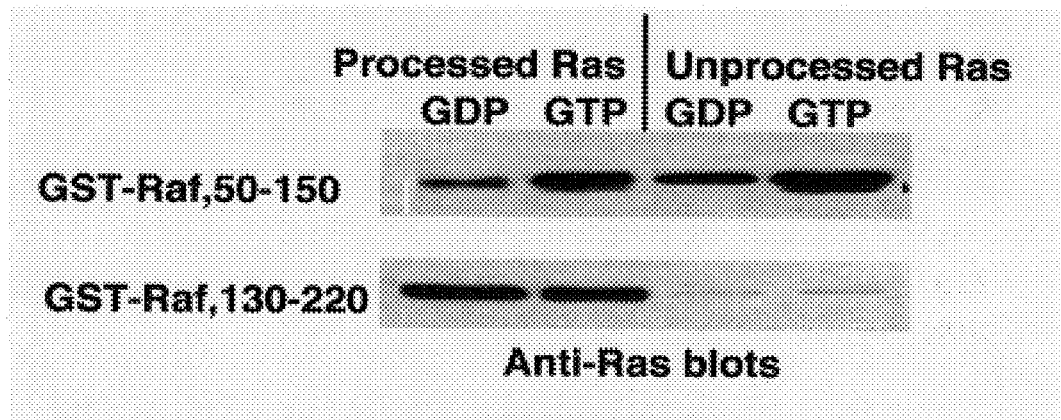

FIG. 7A is an immunoblot showing that binding of a zinc finger domain-containing Raf fusion protein (GST-Raf, 130–220), containing amino acids 130–220 of Raf (FLDHVPLTTHNFARKTFLKLAFCDICQKFLLNGFRC QTCGYKFHEHCSTKVPTMCVDWSNIRQLLLFPNS TIGDSGVPALPSLTMRRMRES; SEQ ID NO:18) to Ras is not GTP-dependent but rather dependent on Ras-farnesylation. In contrast, binding of a Raf fusion protein containing the primary Ras binding site, GST-Raf, 50–150 which contains amino acids 50–150 of Raf (DPSKTSNTIRVFLPNKQRTVVNVRNGMSLHDCLM KALKVRGLQPECCAVFRLLHEHKGKKARLDWNTD AASLIGEELQVDFLDHVPLTTHNFARKTFLKLA; SEQ ID NO:5) is GTP-dependent.

Figure 7B:
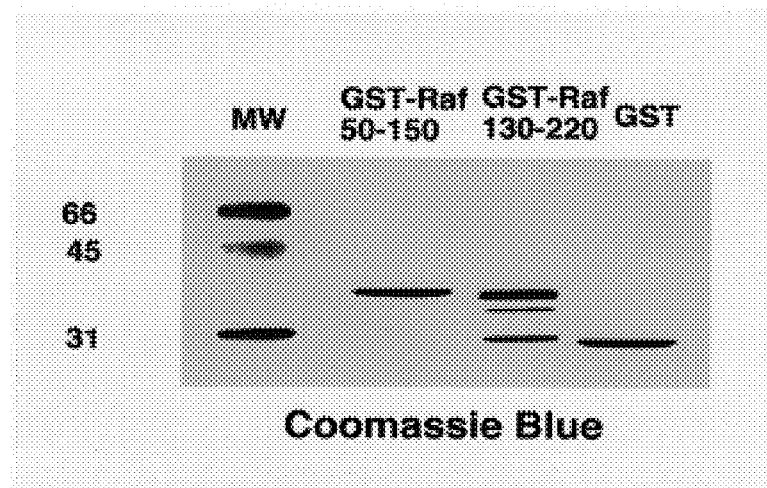

FIG. 7B is a photograph of an electrophoretic gel in which the fusion proteins in FIG. 7A (GST Raf, 50–150 and GST Raf 130–220) were stained with Coomassie Blue.

Raf zinc finger domain has multiple functions in Raf activation

Cell proliferation is the culmination of a successfully transduced intracellular signal, e.g, an intracellular signal transduced via the Ras-mediated signal transduction pathway which can be improperly turned on in many types of cancer. Inhibition of Ras-Raf binding interrupts transduction of an intracellular signal along the Ras signal transduction pathway, and thus, inhibits cell proliferation. The data described herein indicate that inhibition of the Ras-Raf interaction using the compositions and methods of the invention is a promising approach to treating cancer and other diseases characterized by unwanted cell proliferation.

The function of the c-Raf-1 zinc finger domain in the activation of the Raf kinase was analyzed using zinc finger structures which differ from the wild type Raf zinc finger. Mutation of Raf Cys 165/168 to Ser was found to strongly inhibit the Ras dependent activation of c-Raf-1 by EGF. Deletion of the Raf zinc finger and replacement with a homologous zinc finger from PKCγ (γ/Raf) also abrogated EGF-induced activation, but enabled a vigorous PMA-induced activation, which occurs through a Ras-independent mechanism. Although γ/Raf binds PMA, activation of γ/Raf by PMA in situ is indirect, inasmuch as PMA addition in vitro does not activate γ/Raf. The impaired ability of Ras-GTP to activate the Raf zinc finger variants in situ is attributable to at least two factors related to Raf function. One factor is a decrease in Ras binding; both Raf by zinc finger variants exhibited decreased association with Ras (V12) in situ on coexpression in COS cells, as well as diminished binding in vitro to immobilized COS recombinant prenylated Ras (V12)-GTP. In contrast, Raf binding to unprenylated prokaryotic recombinant Ras-GTP is unaffected by Raf zinc finger mutation. The second factor is a decrease in the activation of Raf catalytic function as reflected by transforming activity. Zinc finger mutation (C165, 168S) severely inhibited the Ras-independent transforming activity of Raf CaaX, a potent transforming agent, which is a Ras-independent membrane-bound form of Raf.

The Raf zinc finger plays an important role in the overall binding of Raf to Ras-GTP in situ, and once Raf is recruited to the membrane, an intact zinc finger is necessary for the transition to an active state, perhaps through the binding of a membrane lipid. Zinc finger domain-mediated binding of Raf to Ras leads to Raf activation, a critical event in the cellular signal transduction pathway which culminates in cell proliferation. The Raf zinc finger binds to Ras at an epitope that is available only on prenylated Ras, and is distinct from the effector loop. In addition to its participation in Ras binding, a role for the zinc finger in Raf activation is revealed by the loss of Raf-CaaX transforming activity by mutation of the zinc finger.

Reagents

Phorbol 12, 13 dibutyrate (phorbol myristate acetete; PMA) was purchased from Sigma. EGF was purchased from Calbiochem. Commercially available anti-Myc monoclonal antibodies, e.g., 9B7 and 9E10.2, were employed for immunoprecipitation and immunoblotting. The M2 Flag monoclonal antibody was purchased from Kodak. Enhanced Chemiluminescence (ECL) reagents were obtained from Amersham.

c-Raf-1 was tagged immediately after the initiator methionine. DNA encoding a thirty-three amino acid epitope from human c-Myc was inserted into pMT2. Human c-Ha Ras (V12) was tagged at its aminoterminus with the FLAG epitope (MDYKDDDK; SEQ ID NO:8); DNA encoding the tag was inserted into the vector pCMV5 (Anderson et al., 1989, J. Biol. Chem. 264:8222). The c-Ha Ras, human MEK-1, and rat ERK-1 polypeptides were expressed as GST fusion proteins using the pGEX-KG vector (Guan et al., 1991, Anal. Biochem. 192:262–276). After purification by GSH-sepharose, free ERK-1 was obtained by thrombin cleavage. Human PKCγ cDNA was obtained from ATCC Accession Number 37707.

Mutagenesis of Raf

The site specific mutations in the Raf aminoterminus ($K_{84}$ALK (SEQ ID NO:4) to $A_{84}$AAA (SEQ ID NO:9); C165, 168S) were introduced using the Altered Sites mutagenesis system (Promega). Replacement of the Raf zinc finger domain by the more carboxyterminal of the two zinc fingers of PKCγ (FIG. 1A–1B) was accomplished as follows. The Raf zinc finger domain was first removed by deleting amino acids 150–177 (SEQ ID NO:6). A Raf-1 cDNA fragment encoding amino acids 178–305 was amplified by polymerase chain reaction (PCR); the upstream primer used had the DNA sequence of 5' AGCT AAGCTTGTAGCGGTACCAAAGTACCTACTATG 3' (SEQ ID NO:10), which introduces HindIII and KpnI sites (restriction sites are underlined). The downstream primer used had the DNA sequence of 5' GGGTTTTCGGCTGT-GACCAG 3' (SEQ ID NO:11). The 10 amplified cDNA fragment, cut with HindIII and BstXI, was used to replace a Raf HindIII and BstXI cDNA segment encoding amino acids 149 to 305. Next, the DNA sequences encoding the more carboxyterminal zinc finger domain (amino acids 99 to 152 (SEQ ID NO:7) of human PKCγ were amplified as follows: upstream primer, 5'AGCT AAGCTTCGGAACAAGCACAAGTTCCGT3' (SEQ ID NO:12); downstream primer: 5°CGG GGTACCGCACAGAGAGGGCACGCT3' (SEQ ID NO:13) (Quest et al., 1994, J. Biol. Chem. 269:2961–2970). The amplified PKCγ zinc finger domain was inserted into the Raf (Δ150–177) mutant at the HindIII and KpnI sites to give the γ/Raf chimera shown in FIG. 1A–1B. The Raf mutants were confirmed by DNA sequencing.

The Raf CaaX construct was made by subcloning an EcoRI fragment of a cDNA encoding wildtype c-Raf-1 into pAlter (Promega). The gene was altered to encode a shortened N-terminal Myc epitope (MEEQKLISEEDL; SEQ ID NO:14) and the C-terminal 17 amino acids of K-Ras-4B (KDGKKKKKKSKTKCVIM; SEQ ID NO:15) using the Altered Sites mutagenesis system (Promega). Additional mutations were later introduced in c-Raf-1 using the Myc-Raf CaaX gene as a template. Mutations were confirmed by DNA sequencing and by in vitro translation of the mutant gene using the Promega TNT system. For expression in mammalian cells, DNA encoding Raf CaaX was subcloned as an EcoRI fragment into the pBAB puro vector.

Transient expression, immunoprecipitations and immunoblots

The cDNAs encoding the Myc-tagged c-Raf-1 variants in the mammalian expression vector pMT2, alone or with a FLAG-tagged Ha-Ras (V12) in the vector pCMV5, were transfected into COS M7 cells by the DEAE-dextran method known in the art using a total of 10 µg of the recombinant DNA. For the Ras-Raf coprecipitation experiments, cells were extracted 48 hours after transfection into a lysis buffer containing 50 mM Tris Cl (pH 7.5), 1 mM EDTA, 2 mM EGTA, 1 mM dithiothreitol, 25 mM β-glycerophosphate, 1 mM sodium vanadate, 1% triton X-100, and proteinase inhibitors. For the measurement of Raf kinase activity, the cells were serum-deprived by placement in Dulbeccos modified Eagles minimal essential medium (DMEM) containing 0.1% FBS. Serum-deprivation of cells was commenced 30 hours after the cells were transfected. After an additional 16–18 hours, the cells were treated with 10% FBS, mitogens or carrier (control) prior to lysis.

Immunoprecipitations were conducted for one hour at 4° C. using monoclonal antibody 9B7.3 for Myc-Raf and the M2 anti-FLAG monoclonal antibody for FLAG-Ras. The immune complexes were recovered with protein-G Sepharose and subjected to SDS-polyacrylamide gel electrophoresis followed by electrophoretic transfer to a PVDF membrane. The resolved proteins were visualized by the ECL method known in the art using either anti-Myc monoclonal antibody 9E10.2 or anti-flag antibody M2.

In vitro binding of Raf Variants to Ras

The recombinant GST-Ha-Ras polypeptide was expressed in *E. Coli* and purified on GSH sepharose. COS recombinant FLAG-tagged Ha-Ras (V12) was purified by immunoprecipitation with the M2 anti-FLAG monoclonal antibody and protein-G Sepharose. The immobilized Ras polypeptides were labeled in vitro with S-γ-GTP. COS cell extracts containing recombinant Raf variants were incubated with immobilized Ras at 4° C., for one hour. The complexes were recovered and washed three times in lysis buffer and subjected to immunoblotting.

Raf kinase assay

The kinase activities of the immunoprecipitated Raf variants was assessed using the coupled kinase assay known in the art, e.g., Kyriakis et al., 1993, J. Biol. Chem. 268:16009–16019. The reaction was carried out in a two-stage incubation, in a total volume of 100 µl. In the first stage, the assay mixture contained 25 mM Tris-Cl (pH 7.8), 10 mM $MgCl_2$, 1 mM DTT, 0.1 mM $\gamma^{32}P$-ATP (4000 cpm/pmole), and 2 µg/ml prokaryotic recombinant GST-MEK1. The reaction was initiated at 30° C. by addition of $\gamma^{32}P$-ATP. After 20 min., an aliquot of prokaryotic ERK-1 was added to a final concentration of 10 µg/ml; the incubation was continued for an additional 30 minutes, and terminated by addition of SDS sample buffer. The $^{32}P$ incorporation into GST-MEK1 and ERK1 was detected by autoradiography after SDS-PAGE.

Raf CaaX transformation assay

Rat-1 fibroblasts were maintained in DMEM supplemented with 10% fetal calf serum (GIBCO). Cells grown in a 100 mm dish were transfected with 10 µg of CsCl-purified plasmid DNA using a calcium phosphate transfection kit (GIBCO). On day three, 90% of cells were transferred into a 150 mm dish. One-tenth of the cells were plated in DMEM containing 2.5 µg/ml puromycin. Transfected cultures were incubated at 37° C., 5% CO2 for three weeks. Transformation was evaluated by counting cell foci, an indication of unwanted cell proliferation, and staining the cells with crystal violet. Transfections were standardized by comparing the relative numbers of puromycin-resistant colonies.

Zinc finger domain mutations affect Raf kinase activity

To examine the role of the Raf zinc finger domain in Raf function, two variant zinc finger structures were made. In one, the cysteines at Raf residues 165 and 168 were both converted to serines, thereby mutating both of the tandem $(Cys_3His)$ zinc binding structures. A second variant was constructed by deleting Raf amino acids 150–177 (SEQ ID NO:6) and replacing them with PKCγ amino acids 99–152. PKCγ amino acids 99–152 (SEQ ID NO:7) completely encompass the second, more carboxyterminal of the two PKCγ zinc finger motifs ($H_{102}$ to $C_{151}$), which like the Raf zinc finger is another $(Cys_3His)_2$ structure (FIG. 1B). The expression and regulation of the mutant Raf polypeptides (each of which was tagged at the aminoterminus with a Myc epitope), was examined during transient expression in COS cells. All Raf variants exhibited comparable polypeptide expression, however the level of kinase activity in the mutants differed substantially from the wild type (FIGS. 2A–2D and 3A–3C). Wildtype Raf was strongly activated by treatment of cells with Raf activators, e.g., EGF or PMA, prior to harvest. Mutation of the Raf zinc finger (C165, 168S) resulted in little change in basal Raf kinase activity, but inhibited the EGF and PMA-stimulated activation of Raf kinase by 75–80% (FIGS. 2A–2D). Replacement of the Raf zinc finger domain with the zinc finger domain of PKCγ (γ/Raf) resulted in a slight increase in basal Raf kinase activity, but the response to EGF remained profoundly inhibited. In contrast, phorbol ester, e.g., PMA, increased the MEK kinase activity of γ/Raf to levels comparable to those observed in the EGF/PMA stimulated wildtype Raf (FIGS. 2A–2D and 3A–3C). The PMA activation of γ/Raf is abrogated completely by a double Cys to Ser mutation of the PKCγ zinc finger (FIGS. 2A–2D). The PMA-stimulated activation of γ/Raf was not dependent on endogenous PMA-responsive PKCs. γ/Raf activity remained elevated throughout a 24 hour PMA treatment of transfected COS cells, whereas Myc Raf activity returned to baseline and was unresponsive to readdition of PMA (but not EGF), indicating effective PKC down regulation. Addition of PMA directly to γ/Raf immunoprecipitated from serum-deprived COS cells did not increase γ/Raf activity under conditions in which the rat brain PKC is strongly activated. Thus PMA binding to γ/Raf in situ is necessary, but not sufficient for activation of γ/Raf.

Experiments were conducted to determine whether endogenous Ras was essential for the PMA-stimulated activation of γ/Raf. Mutation of Raf amino acids $K_{84}ALK_{87}$ (SEQ ID NO:4) abolished the ability of a fragment of Raf containing amino acids 1–149 to bind in vitro to prokaryotic Ras-GTP. Introduction of the (84–87A) mutation into wildtype Raf resulted in over 85% inhibition in the EGF or PMA-stimulated activation in COS cells expressing Myc Raf (84–87A) compared to those expressing wildtype Myc Raf (FIGS. 3A–3C). When introduced into γ/Raf, the (84–87A) mutation reduced the residual EGF-stimulated activity by a further 80%, so that the overall activity of the γ/Raf (84–87A) variant in the presence of EGF was less than 5% that of wildtype Raf. In contrast, the activity of γ/Raf (84–87A) in the presence of PMA was approximately 50% that of wildtype Raf (FIGS. 3A–3C). Thus the ability of PMA to activate γ/Raf in situ exhibits little dependence on an interaction between γ/Raf and Ras.

These data indicate that a structurally intact zinc finger is necessary for Raf activation by receptor tyrosine kinases.

Replacement of the Raf zinc finger by a homologous zinc finger structure is not sufficient to restore normal regulation by receptor tyrosine kinases, even though the replacement zinc finger and the Raf catalytic domain are themselves functionally intact.

Effects of zinc finder domain mutations on the binding of Raf to Ras

The loss of EGF-stimulated Raf activation caused by a site mutation or replacement of the Raf zinc finger was found to be almost as severe as the inhibition caused by mutation of Raf residues 84–87 (SEQ ID NO:4) in the Ras-binding domain which binds directly to the effector loop of Ras. The association in situ of Ha Ras (V12) with wildtype and variant Rafs was evaluated by coimmunoprecipitation experiments (FIGS. 4A–4C). Recovery of Myc-Raf (84–87A) with Ha-Ras (V12) was decreased to less than 10% of that of wildtype Myc-Raf. Recovery in the Ras immunoprecipitate of the zinc finger variants Raf (C165/168S) and Myc-γ/Raf was also substantially decreased, to approximately 20–25% of the level observed with wildtype Myc-Raf.

The impaired ability of the Raf zinc finger variants to bind to Ras in situ was confirmed by examination of the binding in vitro (FIGS. 5A–5B). Recombinant v-Ha Ras was expressed alone in COS cells, purified by immunoprecipitation, and incubated in vitro with extracts from COS cells transfected with wildtype Raf, Raf (84–87A), γ/Raf, and a double mutant γ/Raf (84–87A). In parallel to the results observed with coexpression in situ (FIGS. 4A–4C), the binding of γ/Raf to COS recombinant v-Ha Ras in vitro is substantially decreased compared to wildtype Raf, and the binding of Raf (84–87A) to Ras even more so. No binding was detected with the Raf double mutant (FIG. 5A–5B). The impaired binding of Raf zinc finger mutants to Ras was unexpected because binding of GST Raf 1–149 and GST Raf 1–257 to prokaryotic Ras-GTP was essentially indistinguishable.

The ability of COS recombinant Raf, Raf (C165/165S), γ/Raf and Raf (84–87A) to bind in vitro to prokaryotic GST-Ras-GTP was examined (FIGS. 6A–6B). Raf (84–87A) exhibited impaired binding to GST-Ras-GTP compared to the binding observed with wildtype Raf. In contrast, the prokaryotic Ras GTP bound to the zinc finger mutant Rafs at a level comparable to the binding of wildtype Raf. These data indicate that optimal Raf binding to prokaryotic, unprenylated GST-Ras-GTP does not require an intact Raf zinc finger, whereas the binding of Raf to COS recombinant Ras, which undergoes carboxyterminal prenylation and processing in situ, is strongly dependent on the integrity of the Raf zinc finger, whether examined in vitro, or during coexpression in situ.

Effects of zinc finger domain mutation on the biologic activity of Raf CaaX

The role of the Raf zinc finger in Raf activation, e.g., Ras binding and the translocation of Raf to the membrane, was examined. The effects of zinc finger mutation on the ability of Raf CaaX to promote focus formation, i.e., cell proliferation, is shown in TABLE 1.

TABLE 1

Transformation of Raf-1 fibroblasts by Raf CaaX is Significantly Impaired by Mutation of the Zinc Fingers

| Construct | Focus Formation | Raf CaaX Expression |
|---|---|---|
| PBAB puro (vector) | 0 | No |
| Raf CaaX, wildtype | 100 | Yes |
| Raf CaaX, K375M | 0 | Yes |
| Raf CaaX, K84ALK→A84AAA | 64 +/− 23 | Yes |
| Raf CaaX, C165,168S | 15 +/− 12 | Yes |

Rat-1 cells were transfected with 10 μg of pBABpuro plasmid DNA encoding each of the Raf mutants. Foci formation was standardized to wildtype Raf CaaX which was approximately 50% as efficient as HRas (V12) expressed in pBABpuro. Results are the average of five independent experiments.

Raf CaaX has been engineered to express Ki-Ras residues 172 to 188 (SEQ ID NO:15) fused to the Raf carboxyterminus. The Raf CaaX fusion protein undergoes prenylation and other carboxyterminal processing characteristics of Ki-Ras, which are involved in the constitutive localization of Raf CaaX at the cell surface membrane. In contrast to unmodified c-Raf-1, Raf CaaX is a potent transforming agent in rat-1 cells, resulting in focus formation at approximately 50% the rate of oncogenic Ha-Ras (V12). Mutation at the Raf ATP binding site (K375M) completely abolished the transforming activity of Raf CaaX (TABLE 1). Mutations throughout the Raf aminoterminus that abolish the binding of GST Raf 1–149 prokaryotic Ras-GTP in vitro and which strongly inhibit the EGF/PMA activation of wildtype Raf (FIGS. 1A–1B and 2A–2D) had no significant effect on the number of foci formed by Raf CaaX. These data indicate that transformation by Raf CaaX is independent of its ability to bind to the Ras effector domain. In contrast, mutation of the Raf CaaX zinc finger domain inhibited focus formation by 85% (TABLE 1). This result suggests that a structurally intact zinc finger domain is necessary for Raf kinase activity in situ, irrespective of prior Raf recruitment to the plasma membrane.

Raf protein domains involved in binding to Ras

The manner in which Raf interacts with Ras was characterized. Binding assays, competitive co-precipitation assays, and kinase assays were used to measure Ras-Raf binding and activation of Raf kinase.

The consequences of Raf zinc finger mutation, e.g, site mutations or replacement of the Raf zinc finger with the PKC zinc finger) are not due to a propagated disturbance in the folding of other important functional domains in the Raf polypeptide. The integrity of the Raf catalytic domain was verified in the γ/Raf mutant, the kinase activity of which, although poorly responsive to EGF, is activated fully by PMA. This result also validates the functional integrity of the PKCγ zinc finger, expressed as a fusion within the Raf polypeptide. The functional integrity of the aminoterminal Raf segment, residues 50–150 (SEQ ID NO:5), was confirmed by the data shown in FIGS. 6A–6B, which demonstrate that the binding of Raf (C165, 168S) and γ/Raf to prokaryotic GST-Ras-GTP is essentially identical to that of wildtype Raf. Consequently, the altered response of Raf (C165, 168S) and γ/Raf to EGF in situ is attributable to loss of functions provided by the normal Raf zinc finger structure, rather than to disturbances elsewhere in the Raf polypeptide introduced by the mutation.

The mechanisms of PMA activation of wildtype Raf and the γ/Raf are largely distinct. PMA activation of wildtype Raf proceeds through the PMA-induced activation of Ras. Mutation of Raf residues 84–87 (SEQ ID NO:4) in wildtype Raf reduces PMA activation by greater than 85%, whereas such a mutation has less of an impact on PMA activation of γ/Raf. PMA activation of γ/Raf depends on direct binding of PMA to γ/Raf, as evidenced by the abrogation of the activation by mutation of the PKCγ zinc finger within γ/Raf (FIGS. 2A–2D). In contrast, PMA activation of wildtype Raf is entirely indirect; PMA does not bind directly to the Raf zinc finger.

The insertion of the PKCγ zinc finger in place of the normal Raf zinc finger serves both to eliminate the functions of the normal Raf zinc finger, and to introduce a new set of functions, defined by those of the PKCγ zinc finger. One newly acquired function is the ability of γ/Raf to bind PMA directly, thereby enabling the Ras-dependent membrane localization step to be bypassed, at least in the presence of PMA; like the addition of a CaaX motif to Raf, the PKCγ zinc finger enables the recruitment of Raf to the membrane in the presence of PMA to proceed in a Ras-independent fashion. The binding of PMA to γ/Raf in itself does not directly activate Raf, but like the addition of CaaX to the Raf carboxyterminus, the PKCγ zinc finger enables the steps necessary for Raf activation to proceed effectively.

As discussed above, the Raf zinc finger structure participates in the regulation of the Raf kinase activity in at least two ways. First, the Raf zinc finger is critical for the high affinity association of Raf with Ras in situ. The interaction of the Raf zinc finger with Ras appears to be independent of the interaction between the Ras effector loop and the more aminoterminal Raf segment (amino acids 50–150). The latter interaction is disrupted by mutation of Raf residues 84–87, which greatly reduces the binding in vitro of Raf to prokaryotic, unprenylated GST-Ras-GTP. In contrast, mutation in, or replacement of the Raf zinc finger does not detectably alter Raf binding to prokaryotic GST-Ras-GTP, but only to eukaryotically expressed, prenylated Ras.

The site on Ras to which the Raf zinc finger binds involves Ras residues, e.g., Ras N26, V45, that flank the effector loop. Ras prenylation also contributes to the binding of Ras with the Raf zinc finger. The contribution to Ras-Raf binding from the Raf zinc finger likely increases the avidity of Raf binding to the membrane, either to Ras itself or to acidic phospholipids in the membrane inner leaflet. In addition, the Raf zinc finger participates in the steps that lead to activation of Raf catalytic function.

A second function of the zinc finger in the transition of Raf from inactive to an active state is indicated by the inhibitory effect of zinc finger mutation on the transforming action of Raf CaaX. Fusion of the carboxyterminal CaaX motif from Ki-Ras onto c-Raf is sufficient to target Raf to the plasma membrane, where it undergoes a Ras-independent activation, and is capable of Ras-independent transformation of rat-1 cells. Mutation of the zinc finger markedly impairs the transforming activity of Raf Caax (TABLE 1). These results indicate that once at the plasma membrane, an intact Raf zinc finger is required for a subsequent step in Raf activation. The binding of PMA may induce a conformational change in γ/Raf that enables γ/Raf to be converted to an active state through a covalent modification (e.g., a site specific phosphorylation or acylation) of the γ/Raf polypeptide. The Raf zinc finger may also mediate an analogous step in the activation of membrane-bound Raf CaaX, as well as in the activation of wildtype c-Raf-1 bound to Ras-GTP in situ The role of the Raf zinc finger in Raf activation involves the binding of the zinc finger to a membrane associated lipid, e.g., the farnesyl moiety of Ras itself. Engagement of the Raf zinc finger by the prenyl moiety or another membrane lipid induces a conformational change in c-Raf-1 that enables a further, covalent modification which results in stable activation of Raf catalytic activity. The direct binding of the Ras prenyl structure or other lipids to Raf is a crucial step in c-Raf-1 activation. The Raf zinc finger domain binds to an epitope present only in prenylated Ras.

FIGS. 7A–B show that a bacterial recombinant fusion protein (GST, Raf 130–220) that encompasses the Raf zinc finger domain (SEQ ID NO:2) binds strongly to processed (i.e., farnesylated) baculoviral (BV) recombinant H-Ras but very poorly to unprocessed (i.e., unfarnesylated) BV H-Ras. These data indicate that zinc finger domain-mediated Ras-Raf binding is dependent on Ras farnesylation, i.e., Ras processing, (and is not GTP-dependent). In contrast, the association of Raf amino acids 50–150 (SEQ ID NO:5) to the Ras effector loop (Ras residues 32–40; SEQ ID NO:3) is GTP-dependent.

Therapeutic applications

The methods of the invention are useful in treating diseases characterized by unwanted proliferation of cells. The invention provides methods of inhibiting Ras-Raf binding interaction by administering compounds, e.g., inhibitory fragments of Ras or Raf (or analogs thereof), or small molecules the structure of which is modeled after the structure of inhibitory polypeptides.

A "fragment" will ordinarily be at least about 10 amino acids, usually about 20 contiguous amino acids, preferably at least 40 contiguous amino acids, more preferably at least 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

Analogs can differ from the native peptides of Ras or Raf by amino acid sequence, or by modifications which do not affect the sequence, or by both. Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the peptide's biological activity.

Modifications (which do not normally alter primary sequence) include in vivo or in vitro chemical derivitization of peptides, e.g., acetylation or carboxylation. Also included are modifications of glycosylation, e.g., those made by modifying the glycosylation patterns of a peptide during its synthesis and processing or in further processing steps, e.g., by exposing the peptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Modification of these peptides to improve penetration of the blood-brain barrier would also be useful. Peptides may be altered to increase lipophilicity (e.g. by esterification to a bulky lipophilic moiety such as cholesteryl) or to supply a cleavable "targetor" moiety that enhances retention on the brain side of the barrier (Bodor et al., Science 1992, vol. 257, pp. 1698–1700). Alternatively, the peptide may be linked to an antibody specific for the transferrin receptor, in order to exploit that receptor's role in transporting iron across the blood-brain barrier (Friden et al., Science, 1993, vol. 259, pp. 373–377).

Peptides may be administered to the patient intravenously in a pharmaceutically acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

Since blocking the association of Ras with Raf interferes with receptor-mediated activation of immune cells, this method may also be useful in downregulating the immune response in patients with autoimmune diseases such as systemic lupus erythematosus (SLE), type 1 diabetes, and rheumatoid arthritis. Suppression of an immune response using this method may also be useful in the treatment of allograft or xenograft recipients to prevent rejection of a transplanted organ.

Therapeutic administration of a peptide intracellularly can also be accomplished using gene therapy, wherein a nucleic acid which includes a promoter operatively linked to a sequence encoding a heterologous peptide is used to generate high-level expression of the peptide in cells transfected with the nucleic acid. DNA or isolated nucleic acid encoding peptides of the invention may be introduced into cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule in the case of gene therapy.

Compounds that inhibit the interaction of Ras with Raf

Investigations of the respective binding surfaces of the Raf and Ras proteins has shown that in addition to the binding of the Ras effector loop (amino acids 32–40) to Raf amino acids 50–150, the Raf zinc finger domain is essential for Ras-Raf binding. Inhibitory peptides, can be used as models to synthesize therapeutic compounds which inhibit Ras/Raf interaction in vitro and in vivo. Such modeling techniques are known in the art of synthetic chemistry.

For example, small, overlapping sets of amino acid peptides which span the regions of Raf residues 50–150 and 139–184 and Ras residues 32–40 can be synthesized and screened for inhibitory activity. Peptides found to inhibit Ras-Raf interaction can then be used as structural prototypes for the synthesis of conformationally constrained analogs. Peptide bonds within the analogs can be modified or replaced to yield potent, stable, non-peptidyl inhibitors suitable for therapy.

The crystal structure of Ras is known in the art and can thus be used to derive the actual conformation of binding residues. Similarly, X-ray crystallography of Raf crystals and Ras/Raf co-crystals can be used to predict the inhibitory structure of each inhibitory peptide. The structure of the Raf-derived inhibitory peptides can be used to formulate smaller non-peptidyl compounds which mimic essential aspects of the interactive peptide structure. The inhibitory activity of these candidate compounds can then be confirmed using the methods of the invention.

Co-crystals of peptide-Ras and peptide-Raf can be analyzed using X-ray crystallography and nuclear magnetic resonance analysis to determine the structure of the inhibitory peptide in its bound state. Inhibitory peptides can also be characterized by physical chemistry techniques, e.g., circular dichroism, fluorescence, electron spin resonance, that yield data concerning the local environment of the peptides interacting with the protein. Synthetic chemistry techniques can then be used as described above to produce compounds which mimic the inhibitory conformation of each peptide.

Screening assays

The invention can also be used to screen a candidate compound for the ability to inhibit the interaction of Ras with Raf.

Candidate compounds can be evaluated for anti-proliferative activity by contacting Raf or a Ras-binding fragment thereof, e.g., a zinc finger domain-containing fragment of Raf, with a candidate compound and determining binding of the candidate compound to the peptide, or Ras-Raf binding. Raf or Ras-binding fragment of Raf can be immobilized using methods known in the art such as binding a GST-Raf fusion protein to a polymeric bead containing glutathione. Binding of the compound to the Raf peptide is correlated with the ability of the compound to disrupt the signal transduction pathway and thus inhibit cell proliferation.

A co-precipitation competition assay can also be used to measure the relative binding affinities of Ras or fragments and mutants thereof for Raf and fragments and mutants thereof. The effect of various candidate compounds to disrupt or reduce binding can also be measured in such a competition assay.

Candidate compounds can be screened for the ability to bind to Ras or a Raf-binding fragment of Ras. Similarly, compounds can be screened as above for the ability to bind to Raf to identify a compound with anti-proliferative activity.

In another screening method, one of the components of the Ras-Raf binding complex, such as Ras or a Raf-binding fragment of Ras or Raf or a Ras-binding fragment of Raf, is immobilized. Peptides can be immobilized using methods known in the art, such as adsorption onto a plastic microtiter plate or specific binding of a GST-fusion protein to a polymeric bead containing glutathione. For example, GST-Raf or GST-Ras can be bound to glutathione-Sepharose beads. The immobilized peptide is then contacted with the labeled peptide to which it binds (Ras in this case) in the presence and absence of a candidate compound. Unbound peptide can then be removed and the complex solubilized and analyzed to determine the amount of bound labeled peptide. A decrease in binding is an indication that the candidate compound inhibits the interaction of Ras with Raf.

A variation of the above-described screening method can be used to screen for another class of candidate compounds which are capable of disrupting a previously-formed Ras-Raf interaction. In this example, a complex comprising Ras or a Raf-binding fragment thereof bound to Raf or a Ras-binding fragment thereof is immobilized as described above and contacted with a candidate compound. The dissolution of the complex by the candidate compound correlates with the ability of the candidate compound to disrupt or inhibit the interaction of Ras with Raf.

Another screening method involves measuring Raf activation or Raf catalytic activity, e.g., Raf kinase activity, in the presence and absence of a candidate compound. A decrease in Raf activation in the presence of the compound compared to that in its absence is an indication that the candidate compound inhibits Raf activation, and therefore, signal transduction along the Ras-Raf pathway.

In yet another screening assay, candidate compounds can be screened for the ability to inhibiting cell proliferation by providing a cell transfected with DNA encoding a transformation-competent Ras such as Ha-Ras (V12), Ras CaaX, or myristoylated Ras (Cadwallader et al., 1994, Mol. Cell. Biol. 14:4722–4730); contacting the cell with a candidate compound; and determining the amount of proliferation of the cell. Cells transfected with transformation-competent proliferate to form foci in culture. A decrease the number of foci in the presence of the candidate compound compared to that in the absence of the candidate compound indicates that the candidate compound inhibits cell proliferation.

Raf CaaX and myristoylated Raf are Ras-independent, i.e., these constructs do not require the effector loop of Ras to localize to the cell membrane. Thus, using cells transfected with DNA encoding Raf CaaX or aminoterminal myristoylated Raf in the screening assay identifies compounds that disrupt the function of the zinc finger in Raf activation which results in a decrease in foci formation or cell proliferation.

Other embodiments are within the following claims.

What is claimed is:

1. A method of reducing proliferation of cells in a mammal, said method comprising administering to said mammal, or contacting said cells with, a compound which inhibits lipid-dependent direct binding of a non-effector loop domain of Ras with a Raf zinc finger domain comprising SEQ ID NO:1, independent of inhibiting direct binding of a Ras effector loop domain comprising SEQ ID NO:3 with a Raf domain comprising SEQ ID NO:5.

2. The method of claim 1, wherein said compound is a peptide mimetic.

3. The method of claim 1, wherein said compound reduces Raf enzymatic activity.

4. The method of claim 1, wherein said mammal is a human.

5. A method of reducing proliferation of cells in a mammal, said method comprising administering to said mammal, or contacting said cells with, a compound which inhibits direct binding of a non-effector loop domain of Ras with a zinc finger domain of Raf comprising SEQ ID NO:1, wherein said compound comprises a lipophilic moiety which binds to a zinc finger domain of Raf.

6. The method of claim 5, wherein said lipophilic moiety is a farnesyl moiety.

7. The method of claim 6, wherein said compound comprises a carboxyterminal fragment of Ras comprising a farnesyl moiety at position $C_{186}$.

* * * * *

UNITED STATES PATENT AND TRADEMARK OFFICE
CERTIFICATE OF CORRECTION

PATENT NO. : 6,103,692
DATED : August 15, 2000
INVENTOR(S) : Joseph Avruch, Zhujun Luo and Mark S. Marshall It is certified that error appears in the above-identified patent and that said Letters Patent is hereby corrected as shown below:

<u>Column 6,</u>
Line 43, after "The" delete [10]

<u>Column 9,</u>
Line 6, after "zinc" delete [finder] and insert -- finger --.

Signed and Sealed this

Twenty-sixth Day of February, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

PATENT NO.     : 6,103,692
DATED          : August 15, 2000
INVENTOR(S)    : Joseph Avruch, Zhujun Luo and Mark S. Marshall It is certified that error appears in the above-identified patent and that said Letters Patent is hereby corrected as shown below:

<u>Title page,</u>
Item [73], Assignee, please add -- and Indiana University, Bloomington, Indiana --.

Signed and Sealed this

Seventeenth Day of August, 2004

JON W. DUDAS
*Acting Director of the United States Patent and Trademark Office*

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
       (A) LENGTH: 46 amino acids
       (B) TYPE: amino acid
       (D) TOPOLOGY: linear (ii) MOLECULE TYPE: None (xi) SEQUENCE DESCRIPTION: SEQ ID NO:1:

```
His Xaa Xaa Xaa Xaa Xaa Xaa Xaa Xaa Xaa Xaa Xaa Xaa Cys Xaa Xaa
 1               5                  10                  15

Cys Xaa Xaa Xaa Xaa Xaa Xaa Xaa Xaa Xaa Cys Xaa Xaa Cys Xaa Xaa
            20                  25                  30

Xaa Xaa His Xaa Xaa Cys Xaa Xaa Xaa Xaa Xaa Xaa Xaa Cys
        35                  40                  45
```

(2) INFORMATION FOR SEQ ID NO:2:

(i) SEQUENCE CHARACTERISTICS:
       (A) LENGTH: 46 amino acids
       (B) TYPE: amino acid
       (D) TOPOLOGY: linear (ii) MOLECULE TYPE: None (xi) SEQUENCE DESCRIPTION: SEQ ID NO:2:

```
His Asn Phe Ala Arg Lys Thr Phe Leu Lys Leu Ala Phe Cys Asp Ile
 1               5                  10                  15

Cys Gln Lys Phe Leu Leu Asn Gly Phe Arg Cys Gln Thr Cys Gly Tyr
            20                  25                  30
```

```
Lys Phe His Glu His Cys Ser Thr Lys Val Pro Thr Met Cys
            35                  40                  45
```

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: linear (ii) MOLECULE TYPE: None (xi) SEQUENCE DESCRIPTION: SEQ ID NO:3:

```
Tyr Asp Pro Thr Ile Glu Asp Ser Tyr
1               5
```

(2) INFORMATION FOR SEQ ID NO:4:

(i) SEQUENCE CHARACTERISTICS:
        (A) LENGTH: 4 amino acids
        (B) TYPE: amino acid
        (D) TOPOLOGY: linear (ii) MOLECULE TYPE: None (xi) SEQUENCE DESCRIPTION: SEQ ID NO:4:

```
Lys Ala Leu Lys
1
```

(2) INFORMATION FOR SEQ ID NO:5:

(i) SEQUENCE CHARACTERISTICS:
        (A) LENGTH: 101 amino acids
        (B) TYPE: amino acid
        (D) TOPOLOGY: linear (ii) MOLECULE TYPE: None (xi) SEQUENCE DESCRIPTION: SEQ ID NO:5:

```
Asp Pro Ser Lys Thr Ser Asn Thr Ile Arg Val Phe Leu Pro Asn Lys
1               5                   10                  15

Gln Arg Thr Val Val Asn Val Arg Asn Gly Met Ser Leu His Asp Cys
            20                  25                  30

Leu Met Lys Ala Leu Lys Val Arg Gly Leu Gln Pro Glu Cys Cys Ala
            35                  40                  45

Val Phe Arg Leu Leu His Glu His Lys Gly Lys Lys Ala Arg Leu Asp
            50                  55                  60

Trp Asn Thr Asp Ala Ala Ser Leu Ile Gly Glu Glu Leu Gln Val Asp
65                  70                  75                  80

Phe Leu Asp His Val Pro Leu Thr Thr His Asn Phe Ala Arg Lys Thr
                85                  90                  95

Phe Leu Lys Leu Ala
            100
```

(2) INFORMATION FOR SEQ ID NO:6:

(i) SEQUENCE CHARACTERISTICS:
        (A) LENGTH: 28 amino acids
        (B) TYPE: amino acid
        (D) TOPOLOGY: linear (ii) MOLECULE TYPE: None (xi) SEQUENCE DESCRIPTION: SEQ ID NO:6:

```
Ala Phe Cys Asp Ile Cys Gln Lys Phe Leu Leu Asn Gly Phe Arg Cys
 1               5                  10                  15

Gln Thr Cys Gly Tyr Lys Phe His Glu His Cys Ser
                20                  25
```

(2) INFORMATION FOR SEQ ID NO:7:

(i) SEQUENCE CHARACTERISTICS:
        (A) LENGTH: 55 amino acids
        (B) TYPE: amino acid
        (D) TOPOLOGY: linear (ii) MOLECULE TYPE: None (xi) SEQUENCE DESCRIPTION: SEQ ID NO:7:

```
Arg Asn Lys His Lys Phe Arg Leu His Ser Tyr Ser Ser Pro Thr Phe
 1               5                  10                  15

Cys Asp His Cys Gly Ser Leu Leu Tyr Gly Leu Val His Gln Gly Gly
                20                  25                  30

Met Lys Cys Ser Cys Cys Glu Met Asn Val His Arg Arg Cys Val Arg
            35                  40                  45

Ser Val Pro Ser Leu Cys Gly
        50                  55
```

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: None (xi) SEQUENCE DESCRIPTION: SEQ ID NO:8:

```
Met Asp Tyr Lys Asp Asp Asp Lys
 1               5
```

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: linear (ii) MOLECULE TYPE: None (xi) SEQUENCE DESCRIPTION: SEQ ID NO:9:

```
Ala Ala Ala Ala
 1
```

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

AGCTAAGCTT GTAGCGGTAC CAAAGTACCT ACTATG          36

(2) INFORMATION FOR SEQ ID NO:11:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

GGGTTTTCGG CTGTGACCAG                                                    20

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

AGCTAAGCTT CGGAACAAGC ACAAGTTCCG T                                       31

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

CGGGGTACCG CACAGAGAGG GCACGCT                                            27

(2) INFORMATION FOR SEQ ID NO:14:

(i) SEQUENCE CHARACTERISTICS:
        (A) LENGTH: 12 amino acids
        (B) TYPE: amino acid
        (D) TOPOLOGY: linear (ii) MOLECULE TYPE: None (xi) SEQUENCE DESCRIPTION: SEQ ID NO:14:

Met Glu Glu Gln Lys Leu Ile Ser Glu Glu Asp Leu
 1               5                  10

(2) INFORMATION FOR SEQ ID NO:15:

(i) SEQUENCE CHARACTERISTICS:
        (A) LENGTH: 17 amino acids
        (B) TYPE: amino acid
        (D) TOPOLOGY: linear (ii) MOLECULE TYPE: None (xi) SEQUENCE DESCRIPTION: SEQ ID NO:15:

Lys Asp Gly Lys Lys Lys Lys Lys Ser Lys Thr Lys Cys Val Ile
 1               5                  10                  15

Met (2) INFORMATION FOR SEQ ID NO:16:

(i) SEQUENCE CHARACTERISTICS:
        (A) LENGTH: 52 amino acids
        (B) TYPE: amino acid -continued (D) TOPOLOGY: linear (ii) MOLECULE TYPE: None (xi) SEQUENCE DESCRIPTION: SEQ ID NO:16:

```
His Asn Phe Ala Arg Lys Thr Phe Leu Lys Leu Ala Phe Cys Asp Ile
1               5                   10                  15

Cys Gln Lys Phe Leu Leu Asn Gly Phe Arg Xaa Xaa Xaa Xaa Cys Gln
            20                  25                  30

Thr Cys Gly Tyr Lys Phe His Glu His Cys Ser Thr Lys Val Pro Thr
        35                  40                  45

Met Cys Val Asp
50
```

(2) INFORMATION FOR SEQ ID NO:17:

(i) SEQUENCE CHARACTERISTICS:
        (A) LENGTH: 57 amino acids
        (B) TYPE: amino acid
        (D) TOPOLOGY: linear (ii) MOLECULE TYPE: None (xi) SEQUENCE DESCRIPTION: SEQ ID NO:17:

```
Leu Arg Asn Lys His Lys Phe Arg Leu His Ser Tyr Ser Ser Pro Thr
1               5                   10                  15

Phe Cys Asp His Cys Gly Ser Leu Leu Tyr Gly Leu Val His Gln Gly
            20                  25                  30

Met Lys Cys Ser Cys Cys Glu Met Asn Val His Arg Arg Cys Val Arg
        35                  40                  45

Ser Val Pro Ser Leu Cys Gly Val Asp
50                  55
```

(2) INFORMATION FOR SEQ ID NO:18:

(i) SEQUENCE CHARACTERISTICS:
        (A) LENGTH: 91 amino acids
        (B) TYPE: amino acid
        (D) TOPOLOGY: linear (ii) MOLECULE TYPE: None (xi) SEQUENCE DESCRIPTION: SEQ ID NO:18:

```
Phe Leu Asp His Val Pro Leu Thr Thr His Asn Phe Ala Arg Lys Thr
1               5                   10                  15

Phe Leu Lys Leu Ala Phe Cys Asp Ile Cys Gln Lys Phe Leu Leu Asn
            20                  25                  30

Gly Phe Arg Cys Gln Thr Cys Gly Tyr Lys Phe His Glu His Cys Ser
        35                  40                  45

Thr Lys Val Pro Thr Met Cys Val Asp Trp Ser Asn Ile Arg Gln Leu
    50                  55                  60

Leu Leu Phe Pro Asn Ser Thr Ile Gly Asp Ser Gly Val Pro Ala Leu
65                  70                  75                  80

Pro Ser Leu Thr Met Arg Arg Met Arg Glu Ser
                85                  90
```